United States Patent
Rasmussen

(10) Patent No.: US 6,565,517 B1
(45) Date of Patent: May 20, 2003

(54) APPARATUS AND METHODS FOR RHINOMANOMETRY

(75) Inventor: Steen Brabrand Rasmussen, Lynge (DK)

(73) Assignee: Rhinometrics A/S, Lynge (DK)

( * ) Notice: Subject to any disclaimer, the term of this patent is extended or adjusted under 35 U.S.C. 154(b) by 0 days.

(21) Appl. No.: 09/744,392

(22) PCT Filed: Jul. 26, 1999

(86) PCT No.: PCT/DK99/00420

§ 371 (c)(1), (2), (4) Date: Jan. 24, 2001

(87) PCT Pub. No.: WO00/06020

PCT Pub. Date: Feb. 10, 2000

(30) Foreign Application Priority Data

Jul. 29, 1998 (DK) .......................... 1998 00989

(51) Int. Cl.[7] ............................... A61B 5/00
(52) U.S. Cl. .................. 600/529; 600/533; 600/538; 600/561
(58) Field of Search ................. 600/529, 533, 600/538–540, 561

(56) References Cited

U.S. PATENT DOCUMENTS 4,326,416 A * 4/1982 Fredberg ................ 600/533
4,602,644 A * 7/1986 DiBenedetto et al. ........ 600/538
5,279,304 A * 1/1994 Einhorn et al. ............. 600/538
5,316,002 A * 5/1994 Jackson et al. ............. 600/538
6,155,986 A * 12/2000 Bryndon et al. ............ 600/538
6,183,423 B1 * 2/2001 Gaumond et al. .......... 600/538

FOREIGN PATENT DOCUMENTS

DE 2719900 10/1978
DE 3120135 12/1982

* cited by examiner

Primary Examiner—Robert L. Nasser
(74) Attorney, Agent, or Firm—Dykema Gossett PLLC

(57) ABSTRACT

The invention relates to an apparatus for determining the pressure drop over the nose of a patient during breathing and determining the opening pressure for the patients Eustachian tube. The apparatus comprises a measuring tube having a proximal end for connecting to a patients nose and a distal end leading to the surrounding atmosphere, a measuring gate, flow measuring means for measuring air flow in the measuring tube, first pressure measuring means for measuring the pressure in the tube proximal end and second pressure measuring means for measuring the pressure at the measuring gate. According to the invention the apparatus comprises means for generating a sound signal in the tube proximal end, or means for generating a sound signal at the measuring gate and means for receiving sound signals in the tube proximal end. The invention further relates to a method for measuring the above mentioned pressure drop.

15 Claims, 2 Drawing Sheets

APPARATUS AND METHODS FOR RHINOMANOMETRY

FIELD OF THE INVENTION

The invention relates to measuring of pressure and pressure drop in a patients nose (rhinomanometry).

BACKGROUND OF THE INVENTION

In the present application the anatomic references have the following meaning:

Nostril: each of the two openings of the nose towards the surroundings, as well as the immediately inside the openings located part of the nose cavities;

Nose cavity: each of the two cavities between the (Septum Nasi) to the rear edge of the nose separation;

Nose separation (Septum Nasi): the separation that separates the two nose cavities;

Cavity behind the rear edge of the nose separation (epipharynx): the cavity located behind the nose separation rear edge and which constitutes the transition between the nose cavities and the throat;

oropharynx: the cavity from the soft plate and down to the branching of the opening (trachea) and the gullet (oesophagus).

Eustachian tube (Tuba): the canal extending from the cavity behind the rear edge of the nose separation of the middle ear.

Rhinomanometry is known examination method for examining flow resistances in the nose. By Rhinomanometry the pressure drop is measured created over each nostril and related nose cavity to (epipharynx) when breathing in and/or out.

These examinations can be active as well as passive (i.e. with or without the patients co-operation, respectively), where the active one has been the most commonly used.

In order to determine the flow resistance over a nostril with related nose cavity it is necessary to determine the pressure difference created from the nostril opening to epipharynx the rear edge of the nose separation (septum nasi) during breathing in or out, simultaneously with the corresponding air flow.

The examination can typically be performed by that the patient breathes via a nose mask or through a measuring tube mounted directly on the one nostril. In the mask, or measuring tube, respectively an apparatus is located which is able to measure the airflow during breathing in or out. The flow measurement can be performed in numerous ways, e.g. as the pressure drop over a known orifice plate or implicitly as the temperature of a heated wire cooled by the airflow.

Rhinomanometry is through the recent more than 25 years typically performed in the following manner for each of the patient's nostrils:

A so-called rhinomanometer comprising a mask with a flow measuring tube mounted thereon is mounted on the nose and a pressure difference transducer in the tube register the pressure drop over an orifice plate, i.e. between the surrounding atmosphere and the inside of the flow tube. The pressure drop created over the orifice plate is hereby an expression for the actual flow. The one side of a second pressure difference transducer opens into the flow measuring tube and its other side opens into a tube, through which the pressure at the rear edge of the nose separation is to be measured.

The pressure at this location (the reference pressure) can be measured through the nostril where flow is not measured via a measuring tube snugly connected to the nostril. Hereby the nose cavity, wherein there is no flow, (and the cavity not occluded by secretion) for determining the pressure at the rear edge of the nose separation to (epipharynx)

This of course has its limitations, as the opposite nose cavity cannot be used as a measuring canal if it is totally or partly clogged.

Alternatively the measuring canal can be established through the mouth, but the pressure in the mouth is only equal to the pressure in the cavity behind the rear edge of the nose separation to (epipharynx), when the soft palate as well as the tongue root (the rear part of the tongue) are in lowered positions, where there is an open passage from the mouth and the throat to epipharynx.

Experience has however shown that it cannot be realized to obtain reliable measurements of the reference pressure through the mouth, as the conditions for doing this is that the patient as mentioned maintains an open passage from the mouth and the throat to epipharynx (by means of the tongue root). By evaluations of it has been concluded that at about 30% of the measurements performed through the mouth, the patient unwillingly closes the passage between the mouth, and the throat to epipharynx, resulting in that these 30% are without value, following the erroneous measurement of the pressure behind the rear edge of the nose separation, where the examiner is not aware of the error.

Furthermore it is a major disadvantage at the hitherto known rhinomanometry examination methods that the function of the Eustachian tubes cannot be monitored. Problems with increased flow resistance in the nose often is connected with problems in the middle ear or with problems in the cavity behind the rear edge of the nose separation (epipharynx), e.g. polyps, which also influence the function of the Eustachian tubes.

It is an objective with the present invention to provide an apparatus, which in different configurations makes far more effective rhinomanometry measurements possible, and which remedies the above mentioned problems and makes possible the measurement of opening pressure for the Eustachian tubes.

SUMMARY OF THE INVENTION

By an apparatus for Rhinomanometry and of the type described above, which corresponds to the introductory part of claim 1, the objective is achieved by means of the features mentioned in the characterizing part of claim 1.

By means of these features it is achieved that the apparatus according to the invention can detect whether there is an acoustic connection between those of a patients respiratory and ear passages to which the apparatus is connected, and thereby implicitly whether there is an opening for pressure equalization and/or air flow between the openings.

With the features mentioned in claim 2 it is achieved that it can be monitored whether there is an acoustical connection from the mouth to the nose, and thereby whether there is a pressure equalizing connection from the mouth to the cavity behind the rear edge of the nose separation.

With the features mentioned in claim 3 it is achieved that it can monitored whether there is an acoustical connection from the nose to the middle ear, and thereby whether there is a pressure equalization connection from the cavity behind the rear edge of the nose separation, through the Eustachian tube to the middle ear.

With the features mentioned in claim 4 it is achieved that the patient himself can establish a pressure in a nose mask or a nose adaptation piece which is connected to the measuring tubes proximal end and thereby built up a pressure in the cavity behind the rear edge of the nose separation, which pressure can provoke the Eustachian tube to open.

With the features mentioned in claim 5 it is achieved that a corresponding pressure can be established from an outer pressure source, which makes it possible that the patient can perform swallowing or chewing movements with a well-defined pressure in the cavity behind the nose separation (epipharynx).

With the features mentioned in claim 6 a corresponding effect is achieved as in connection with claim 2, when the patients second nostril is used as measuring canal, as described above.

With the features mentioned in claim 7 a simplification is achieved, which means that separate microphones are not necessary for sampling the transmitted sound signal. In many rhinomanometers pressure or pressure difference transducers are already present, which have 3 dB crossover frequency at 1 kHz or higher, and which therefore also can measure dynamic pressure changes. Such transducers can immediately be used as microphones, when the sound signal has a frequency of 500 Hz.

With the features mentioned in claim 8 it is achieved in connection with the features mentioned in claim 7 that a known rhinomanometer can be used as an apparatus according to the invention, only adding a battery driven sound generator transducer and one amplifier filter with microphones included related fittings for connection to the relevant tubes of the rhinomanometer.

With the features mentioned in claim 9 a reliable function of the sound signal path in the apparatus according to the invention is achieved, also when relatively high static pressures are present in the patient's respiratory passages.

With the features mentioned in claim 10 an advantageous and automated process is achieved, which can comprise that the examiner and/or the patient by means of sound signals are made aware of whether the required measuring conditions are present.

The invention also relates to a supplementary apparatus as defined in claim 11. By adding the supplementary apparatus to an existing apparatus the same effect as described above may be obtained. The features described above may, where applicable, be applied to this part of the invention.

It is a second objective of the present invention to provide for the mentioned measurements:

This objective is achieved with the features mentioned in claims 12–17.

With the features mentioned in claim 12 a reliable detecting of whether the patient has lifted the tongue root and/or the soft palate is achieved, and thereby clogged the measuring canal extending through the mouth. When this canal is clogged, the acoustical signal path is simultaneously blocked, which immediately can be detected by the significantly drop in level of the acoustic signal.

With the features mentioned in claim 13 advantages corresponding to those mentioned in connection with claim 10.

With the features mentioned in claim 14 a reliable detecting of whether the passage between the patients second nose cavity and second nostril is clogged.

With the features mentioned in claim 15 advantages corresponding to those mentioned in connection with claim 10.

With the features mentioned in claim 16 a reliable detecting of whether the Eustachian tube is open or closed, which is not possible with the prior art.

With the features mentioned in claim 17 a reliable determining of the opening pressure for the Eustachian tube, which is likewise not possible with the prior art.

It should be appreciated that by the expression sound signal a broad spectrum of sound signals is meant, including infra sound frequencies as well as ultra sound frequencies.

The invention will in the following be explained more detailed with reference to embodiments shown on the drawings, on which corresponding parts have the same references in both figures, and where:

DESCRIPTION OF THE PREFERRED EMBODIMENTS

In order to determine the flow resistance over the respective nostril and related nose cavity in a patient, it is necessary to determine the pressure difference which during breathing in or out is created from the nostril opening to the rear edge of the nose separation (septum nasi), (epipharynx) simultaneously with the corresponding air flow. That is performed by rhinomanometry using rhinomanometer known per se.

Figure 1:
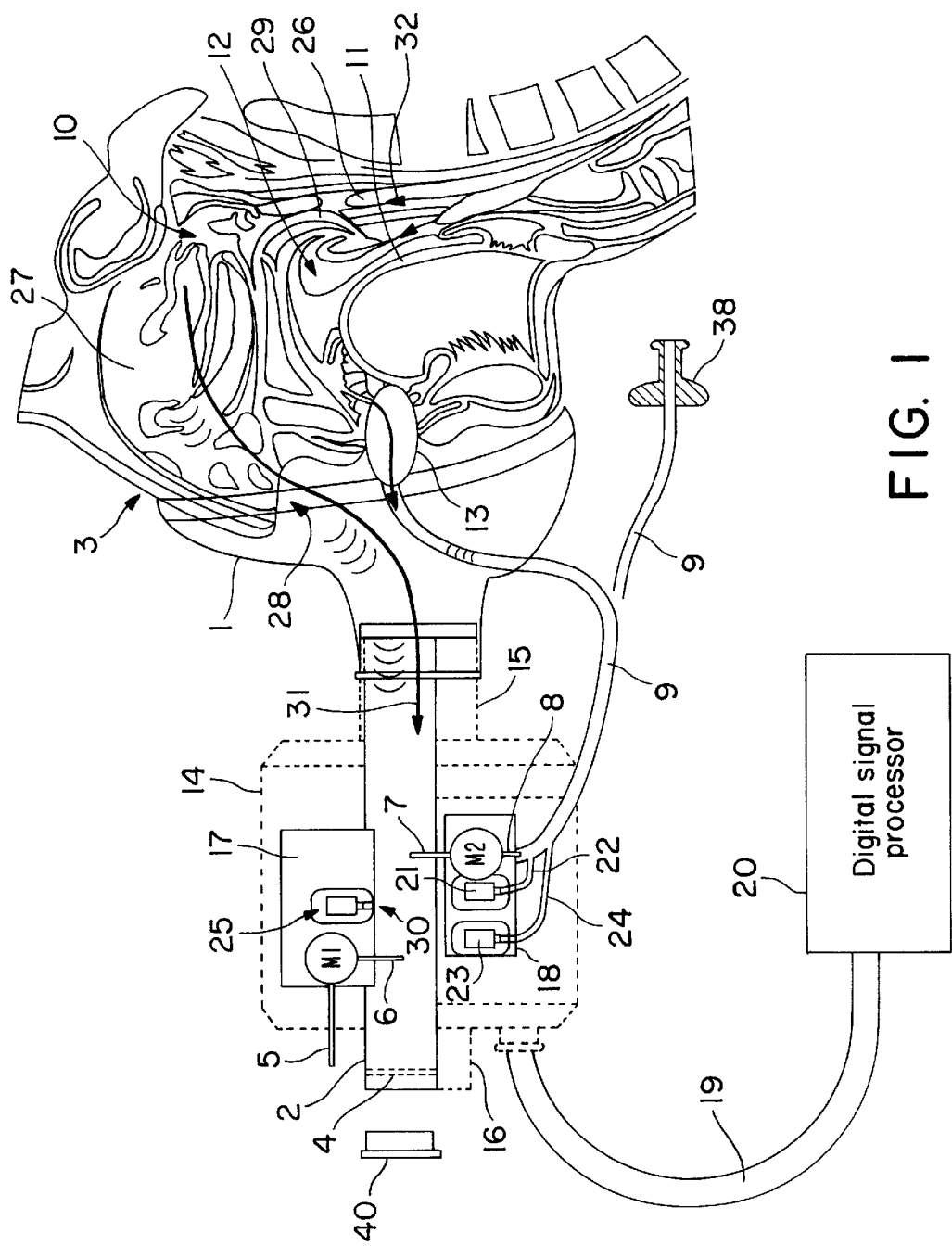
FIG. 1 is a longitudinal cross section showing a rhinomanometer according to the invention during measurement of the nose flow resistance on a patient, with measuring canal for reference pressure through the mouth.

In FIG. 1 an apparatus according to the invention for rhinomanometry is shown. A snug fit mask 1 with a modulated flow measuring tube 2 is placed on the patient's nose and a pressure difference transducer registers the pressure drop which is the present over an orifice plate or a pneumatic resistance 4, the one measuring gate 5 of the transducer is connected to the surrounding atmosphere and the second measuring gate 6 opens into the flow tube 2 interior.

The patient breathes through his/her nose along the path shown with the arrows 32 and 31. The pressure drop created over the orifice plate 4 and measured by the transducer M1 is an expression for the actual flow in the flow tube 2 and thereby for the air flow in the patient's breathing.

The flow tube 2 in the embodiment shown in FIG. 1 is surrounded by a housing 14, indicated by a broken line in FIG. 1, which in its proximal end has a connecting piece 15 for holding the mask 1 and which at its distal end has a connecting piece 16 wherein the measuring tube opens. In the embodiment shown the housing further contains the electronics of the apparatus on two circuit boards 17–18 and is via a cable 19 connected to control unit 20 comprising a computer power supply and more.

A second pressure difference transducer M2 is mounted in such a manner that its one measuring gate 7 opens into the flow measuring tube 2 and its second measuring gate 8 opens into in a pipe or a tube 9 intended for measuring the pressure behind the rear edge of the nose separation (the nose separation is located in the drawing plane and is therefore not shown). Behind the rear edge of the nose separation a cavity 10 (epipharnx) is located, and it is the pressure here that must be measured through the tube 9 as a reference pressure for measuring the pressure drop over the nose.

The reference pressure in the cavity 10 can be measured through the nostril where flow is not measured, by connecting the measuring tube 9 to this second nostril via a sealing around the measuring tube, however the pressure in the mouth is only correct when the tongue root is in a lowered position, meaning that there is an open passage between the mouth and the cavity 10 behind the rear edge of the nose separation.

In the embodiment shown in FIG. 1 the reference pressure is measured through the mouth. The tube 9 is terminated in a mouth adaptation place 13, which the patient holds between the his/her and/or his/her teeth as shown in FIG. 1.

In case of the pressure difference transducer M1 is of such quality that it can sample the sound signal (i.e., that is has an upper crossover frequency which is not significantly lower than the frequency of the sound signal), it can be sufficient to build in a sound emitter such as an electro-acoustic speaker 21 in the housing, which speaker, e.g., is connected to the tube 9 by means of a pipe connection 22.

The sound signal from the speaker 21 will now propagate along the tube 9 through the patient's mouth 12, the throat 25, the cavity 10 behind the rear edge of the nose separation, the nose cavity 27, the nostril 28 and the mask 1 to the flow tube 2, where it will be sampled by the pressure difference transducer M1.

The signal processing program, which processes the pressure measurements in the computer in the control unit, is according to the invention constructed in such a manner that the presence and level of the sound signal is registered and preferably also in such a manner that the pressure and flow measurements that are carried out only are valid when the pressure transducer M1 simultaneously with the registration of pressure receives and recognizes the sound signal from the sound transducer 21.

Furthermore the computer program according to the invention preferably is adapted to control emission of sound signals for information to the examiner and/or the patient, where these signals give information of whether the acoustical signal path is open and thereby whether there is a passage for the reference pressure from the cavity 10 (epipharynx) to one measuring gate 8 of the pressure difference transducer M2. Such signals can according to the invention be adapted for utilization by the patient to train relaxing of the tongue 11 and the soft plate 29 for achieving correct opening of the signal path.

If the pressure difference transducers M1–M2 in the rhinomanometers are not of types which makes possible the sampling of sound signals or if the software which processes the pressure signals cannot be changed for also treating the sound signal, there can according to the invention be built in a sound emitter as a discrete microphone in the apparatus.

This alternative is likewise illustrated in FIG. 1, together with the alternative of transmitting the sound signal in the opposite direction of the one described above. In order to realize this, a speaker 25 is shown the sound opening of which opens directly into the flow tube 2 at the location 30. The sound signal from the speaker 25 propagates along the same signal path as described above, but in the opposite direction to the tube 9, where it via a branch 24 is lead to a microphone 23.

The speaker 25 and/or the microphone 23 can according to the invention be of a type with a vent hole in the membrane, such that their signal function becomes independent from the static pressure in the system. If the software allows, e.g., the speaker signal can be supplied and the microphone signal can be lead away via the connection wires on pressure difference transducers M1–M2.

Figure 2:
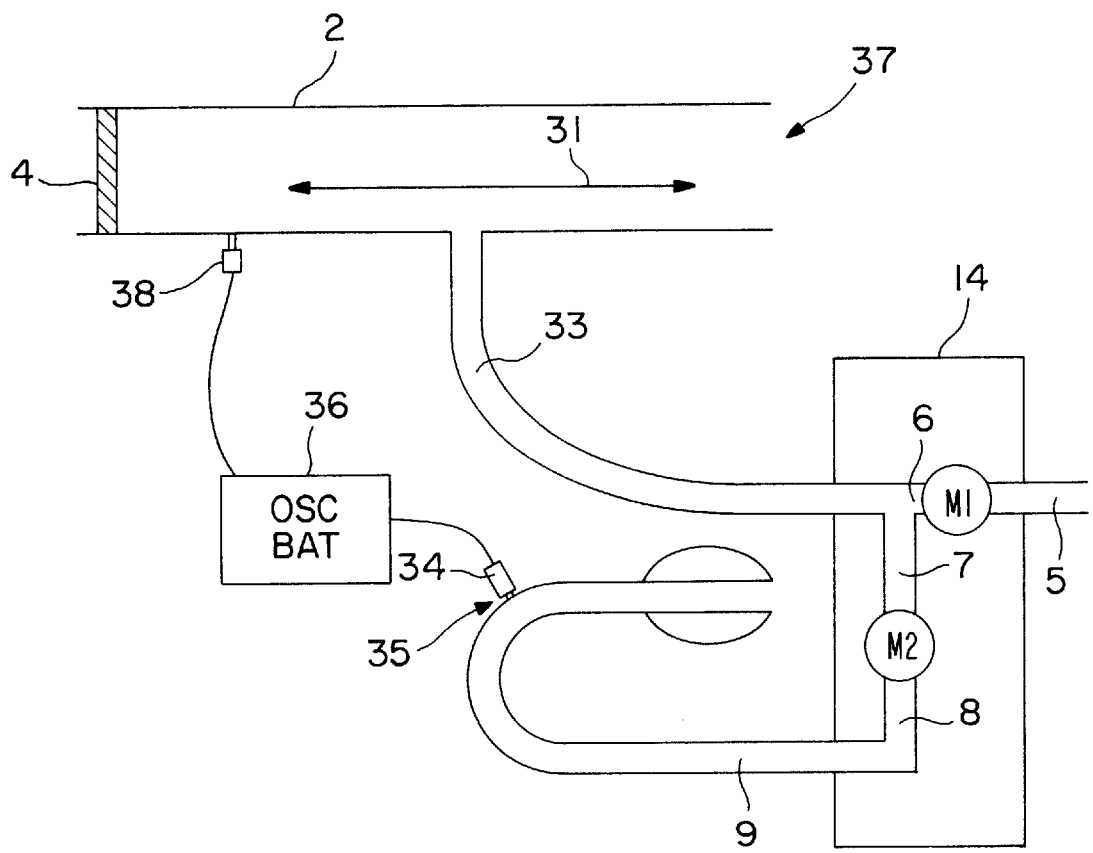
FIG. 2 schematically shows a rhinomanometer of per se known type and with pressure difference transducers with a relatively high crossover frequency, the rhinomanometer being modified according to the invention by adding a battery powered tone generator with a sound transducer.

In FIG. 2 a second embodiment for the apparatus according to the invention is schematically shown. A rhinomanometer of a type known per se comprises a flow tube 2, which at its proximal end 37 is connected to the patient's nose, such at the patient's breathing takes place through the tube 2 in the direction 31. The housing 14, which comprises the electronics of the apparatus, is in the embodiment of FIG. 2 not connected to the flow tube 2 but instead connected to this by means of a pipe 33. The gates 5–8 of the two pressure difference transducers M1–M2 are furthermore connected in the same manner as in FIG. 1. The gate 8 on the transducer hereby connected to a mouth-connecting piece 13, which the patient holds in the mouth during the measurements.

The sound signal is in FIG. 2 injected in the tube 9 by means of a speaker 34 with a special fitting 35 which can fixate by cutting in the tube in a manner not described in more detail. The speaker is driven by a battery-powered oscillator 36, which in the shown embodiment is autonomic and without electrical connection to the rhinomanometer. The sound signal propagates along the tube to the mouth adaptation piece 13, through the patients respiratory passages as described in connection with FIG. 1 to the flow tube 2 and through the tube 33 to the gate 6 of the pressure difference transducers M1, where it is sampled. The device 36, which as mentioned holds an oscillator and a power supply, preferably also comprises an amplifier and relevant filters. A microphone 38 is connected to the device.

The oscillator 36, the speaker 34, the microphone 38, the fitting 35 and suitable software can according to the invention preferably constitute an up-dating package, which can convert a rhinomanometer known per se to an apparatus according to the invention, having the same advantages and field of use as described above in connection with FIG. 1.

According to the invention the apparatuses of FIGS. 1 and 2 be used for detecting the opening of the Eustachian tubes or for measurement of the opening pressure for these.

Again reference is made to FIG. 1. The distal end of the flow measuring tube at the orifice place 4 is closed by means of a plug 40. Hereby the patient can build up an increasing pressure in the respiratory passages by trying to breathe out through the now closed flow tube 2. Furthermore, the mouth-connecting piece 13 is replaced with an ear-connecting piece 38 shown schematically, which is placed in the patient's ear. The sound from the speaker 23 propagates hereby through the tube 9, through the ear, the tympanic membrane and the middle ear via the Eustachian tube to the nose cavity 27 and out in the flow tube 2, where it is sampled by the pressure difference transducer M1.

The sound signal will be attenuated significantly in this signal path if the Eustachian tube is closed and the level of the signal sampled will be an indicator of whether the tube is open.

If instead of the plug 37, a pressure measuring apparatus is mounted to the distal end of the flow tube 2, the construction will at the same time open up a possibility for registration of the pressure necessary for the opening of the Eustachian tube. The pressure measuring apparatus can according to the invention be connected to the computer in the control unit 20, whereby the opening pressure can be registered automatically at the moment the sound signal passes through.

Instead of the patient himself is building up a pressure in the nose, an external pressure source can according to the invention be connected, e.g. together with the pressure measuring apparatus instead of the plug 37. Hereby it is possible to build up an increasing pressure in the mask, controlled by the examiner or the computer. By letting the patient chew or swallow during the increasing pressure the function of the Eustachian tubes can be monitored under more realistic and different conditions, which is not possible with the prior art.

Instead of applying the sound to one ear by means of the build in sound source in the apparatus according to the invention, sound signals can be applied to both ears by means of headphones. If the sound is applied, e.g. with a headphone of the Walkman type to the two ears, the sound can propagate from each ear, the middle ear Eustachian tube and the nose to the flow tube 2. The pressure transducer here registers hereby the opening of the Eustachian tubes. If separation of the measurement result from the right and the left ear is desired two different frequencies can be used for the two ears. The frequencies may be separated by the signal-processing program in the computer.

The examination of children having middle ear problems is a very important part of the work of an ear, nose and throat department. It is therefore of significant importance that alternatives are available during the examination, making children confident with the examination and the examiner.

In order to further make the children confident at such examination, music or speech can be supplied to the headphones when measurements are not performed, hereby distracting the attention of the child, where the music or speech is only interrupted for a few milliseconds where the measurements are performed.

Most Walkman headphones also function satisfactory as dynamic microphones and can therefore also be used in case the direction of the sound signal from the flow tube 2 to the ears.

In this situation a broad specter continuous signal can be supplied from the speaker 25 in the probe housing 14 to the nose 3. The patient is hereby asked to perform swallowing or to drink. At a normal functioning ear and Eustachian tube a short-term opening will occur during each swallowing. The sound signal will hereby propagate through the nose rear part, through the Eustachian tube to the middle ear in the two sides and out through the tympanic membrane to the two as headphones acting as microphones.

At the following signal processing in the measuring system it is hereby possible to determine symmetry in the transmission paths as well as opening time and possible missing opening of one of the signal paths following a malfunction in the Eustachian tube, a cold or middle ear inflammation. This gives the examiner the possibility of performing supplementary examinations of the patient. It is possible with the same equipment to measure several different parameters. Often ear problems is actually nose problems including polyps or mocous membrane problems in the nose.

The apparatuses and the methods according to the invention are therefore a valuable supplement to the examinations, which are performed anyway.

EXAMPLE

Rhinomanometry is a known examination method used over most of the world for examinations of the flow resistance of the nose, where is thereby is important to measure the pressure drop, created over the respective nostrils during breathing out and in.

These examinations have been active as well as passive (the cooperation of the patient), where the active one has been the most often used.

The examination typically comprises that the patient is fitted with a nose mask or has the measuring pipe mounted directly on a nostril. In the measuring tube an apparatus capable of measuring the flow (airflow) during breathing in and out. The flow measurement can be performed in numerous ways, e.g. as the pressure drop over a known orifice plate or a hot wire anemometer.

In order to determine the resistance over the respective nostrils the examiner is forced to determine the pressure created from the individual nostrils opening to the top of the septum (the edge of the nose separation) during breathing in or out, when a suitable flow is present. This has during the passed 25 years typically been performed in the following manner:

1. By means of a mask mounted with a flow measuring tube and a pressure difference transducer between a adaptation piece (plaster) in a nostril, where flow measurement is not desired and the opening (or in the mask the measuring tube) of the one in which the flow measurement is to be performed. See FIG. 1.
2. When the opposite nostril is to be measured the opposite is done.

Under the above mentioned method, the nostril in which there is no flow as a measuring canal in order to determine the pressure at the top of septum.

This has of course its limitations, as the opposite cavity cannot be used if it is totally or partly clogged. When this is the case the examiner is forced to use the mouth as a measuring port in order to determine the pressure over the nostril where flow is present.

Unfortunately it is not possible to obtain reliable measurements through the mouth, as the conditions for this is that the patient holds open the passage between the mouth and the nose with the tongue root. In order to determine these deviations different examinations have been performed, with the purpose of explain this problem. The conclusions have been that about 30% of all these examinations are without value even without the knowledge of the examiner, following incorrect measurements over the nose.

The solution to this problem is according to the invention to add a sound transducer (sound emitter), the output of which opens into the side of the pressure difference transducer which is inserted in the mouth or the nostril opposite of the one where flow measurement is performed.

According to the invention it is convenient that the transducer which measures the pressure drop over the reference orifice plate in the measuring tube is of a type which can measure dynamic pressure changes of up to 1 kHz or higher. See FIG. 1.

The signal processing program, which processes the pressure measurements from the pressure transducer is constructed in such a manner that the measurements performed only are valid if the pressure transducer simultaneously with the registration of a pressure receives and recognizes a signal from the sound transducer through the mouth and out of the nose to the pressure transducer in the flow measuring part.

This means that the examiner at once registers that a blocking in either the nostril where the pressure measurement is desired or that the tongue root closes the passage from the mouth to the top of the nose separation.

Alternative: The sound transducer can alternatively be located at the pressure transducer such that the sound propagates from the flow tube and out of the mouth to the pressure transducer 2. The software hereby utilizes the transducer 1 as reference and 2 as registering unit for the signal.

1. Both pressure transducers are of the type which can also measure dynamic pressure changes and the signal processing part is of such type and quality that it also is capable of comparing the acoustical signal which at an opening at the tongue root or (opposite nostril) can be detected in both transducers.

In this situation it will be sufficient that the acoustical transducer and oscillator as a separate unit is without any other connection to the instrument except for the power supply. As the one side of both pressure transducers opens into the flow tube the acoustical noise which is present here during breathing/respiration be present in both the reference transducer 2 and the flow pressure measuring apparatus 1 with the same level and at correct polarizing, meaning that the pressure transducers can be balanced out.

2. The mask, mouth piece and flow tube can be passive, i.e. be connected by means of calibrated tubes to the instrument where the measurement system is located. Hereby it is possible afterwards to mount a telephone having an oscillator as a battery powered independent unit, which can be connected the patient mouthpiece on existing equipment.

3. Where no or one of the pressure transducers is of a type which is not capable of registering fast dynamic pressure changes, a microphone with a vent channel (a hole in the membrane) can be connected to the rear side for pressure equalization. The signals can from these either be measured discrete or be supplied to the signal paths of the pressure transducers.

Option for measuring the tuba function and opening pressure to the middle ear: an alternative use of this manometer construction is that by inserting a plug in the flow orifice plate and replacing the mouth piece with an ear piece can insert this into the ear of the patient. Hereby it becomes possible to use a rhinomanometer as a measuring system for examinations of the tuba function by measuring whether the tuba opens during swallowing, as the sound from the sound transducer hereby propagates through the ear, via tuba to the nose and out in the flow tube, which is now closed by a plug.

The interesting part is hereby that the construction now at the same time opens up a possibility for measuring the opening pressure which by tuba function problems or middle ear problems is required for opening tuba. This can be performed by the patient himself or instead of the plug in the orifice plate opening supplying an external pressure to the nose.

By building up an increasing pressure in the mask and letting the patient swallow during the increasing pressure the point where tuba opens is reached and hereby the signal path for sound. The pressure that the pressure transducer hereby registers is the pressure, which is present in the top of the nose (epipharynx) in relation to the ear canal or the outside of the tympanic membrane. If the sound transducer is mounted in the flow tube it is possible by mounting an ear adaptation piece in each ear (holding a microphone) to obtain a registration of both tuba passages to the ears, as the opening pressure can vary to the two middle ears.

If the sound is supplied with e.g. a walkman headphone to the two ears and the sound propagates opposite, i.e. middle ear, tuba to nose and flow tube the pressure transducer or the microphone will hereby register the opening of tuba. If it is desired to obtain the separation of the measurement result of the right ear from the left ear two different frequencies can simply be used. These can thereby be separated by the signal-processing program in the measuring system.

It is possible to remove both nose adaptation holders with nose pieces from the measuring tube, inset a plug in the bottom of each holder, replacing nose adaptation pieces with ear adaptation pieces in the holder and inserting these into the patients ears. Another holder without microphone but with nose adaptation piece in the one free tube from the probe housing, placing a plug in the second a supplying a continuous broad specter signal from the transducer in the probe housing to the nose.

The patient is hereafter asked to perform swallowing or to drink some fluid. At a normal functioning ear and tuba function, a short term opening of the tuba occur during the swallowing. The sound signal will hereby propagate through the nose rear part, through tuba (the Eustachian tube) to the middle ear in the two sides and out through the tympanic membrane to the ear adaptation piece and the two microphones. At the following signal processing in the measuring system it is hereby possible to determine symmetry as well as opening time and if one of the signal paths do not open caused by a malfunction in the tuba, a cold or otitis media (middle ear inflammation) This gives the examiner a direct possibility of performing supplementary examinations of the patient. It is possible by means of the same equipment to measure several different parameters. Often ear problem are in fact nose problems, e.g. polyps or mocous membrane problems in the nose. It will therefore be a valuable supplement to the examinations, which are performed anyway.

The examination of children having middle ear problems is a very important part of the work of an ear, nose and throat department. It is therefore a significant importance that alternatives are available at the examination, making the children confident with the examination (the examiner).

Alternatively the examiner can supply the patient with Walkman headphones. Most of these also function satisfactory as dynamic microphones and can hereby be connected as an alternative to maintaining the microphone part.

In order to provide further confidence for a child at such examination, music or speech can be supplied to the headphones (microphones) when measuring is not performed, in order hereby to distract and only interrupt this in the few milliseconds, where the measurements are performed.

Alternatively the signal path can be analyzed in the opposite direction, i.e. with the walkman headphones as a sound source and the microphones in the holder for the nose adaptation piece maintained in the nose, the signals can be sampled in the nose piece when swallowing.

What is claimed is:

1. A device for determining a pressure drop over a nose of a patient during breathing which comprises:
    a first measuring tube having a proximal end for connection to the patient's nose and a distal end leading to a surrounding atmosphere,
    a second measuring tube having a proximal end for connection to the patient's mouth,
    a flow-measuring means for measuring air flow in the first measuring tube, said flow-measuring mean also being capable of sampling a sound signal within said first measuring tube, and
    sound-generating means for generating a sound signal in said second measuring tube for propagation through said second measuring tube, the patient's mouth, throat, rear edge of nose separation, nose cavity and nostril, and then into the first measuring tube for sampling by the flow-measuring means in order to determine whether the patient's throat or nose cavity are blocked.

2. A device according to claim 1, wherein said sound-generating means is an electro-acoustic transducer having a pipe connected to the second measuring tube.

3. A device according to claim 1, wherein said flow measuring means comprises a first pressure transducer having a first measuring gate connected to the first measuring tube and a second measuring gate extending to the surrounding atmosphere.

4. A device according to claim 3, wherein said flow measuring means includes a second pressure transducer having a third measuring gate connected to the first measuring tube and a fourth measuring gate connected to the second measuring tube.

5. A device according to claim 1, including an orifice gate covering said distal end of said first measuring tube.

6. A device for determining a pressure drop over a nose of a patient during breathing which comprises:
   a first measuring tube having a proximal end for connection to the patient's nose and a distal end extending to a surrounding atmosphere,
   a second measuring tube having a proximal end for connection to the patient's mouth,
   a flow measuring means for measuring air flow in the first measuring tube,
   sound-generating means for generating sound in the first measuring tube for propagation through the patient's nostril, nose cavity, rear edge of nose separation, throat and mouth and then into the second measuring tube, and
   sound-detection means for sampling a sound signal in said second measuring tube in order to determine whether the patient's nose cavity or throat are blocked.

7. A device according to claim 6, wherein said sound-generating means is an electro-acoustic transducer.

8. A device according to claim 6, wherein said flow-measuring means comprises a first pressure transducer having a first measuring gate connected to the first measuring tube and a second measuring gate extending to the surrounding atmosphere.

9. A device according to claim 8, wherein said flow-measuring means includes a second pressure transducer having a third measuring gate connected to the first measuring tube and a second measuring gate connected to the second measuring tube.

10. A device for determining opening pressure for a patient's Eustachian tube which comprises:
    a first measuring tube having a proximal end for connection to the patient's nose and a distal end leaving to a surrounding atmosphere,
    a plug closing said distal end of said first measuring tube,
    a second measuring tube having a proximal end for connection to the patient's ear,
    a pressure-measuring means for measuring air pressure in the first measuring tube, said pressure-measuring means being also capable of sampling a sound signal in the first measuring tube, and
    sound-generating means for generating a sound signal in said second measuring tube for propagation through said second measuring tube, the patient's ear, tympanic membrane, middle ear, Eustachian tube, nose cavity and nostril, and then into the first measuring tube, the pressure-measuring means determining air pressure values in the first measuring tube and sampling sound signals in the first measuring tube to determine whether the patient's Eustachian tube is blocked.

11. A device according to claim 10, wherein said sound-generating means is an electro-acoustic transducer having a pipe connected to the second measuring tube.

12. A device according to claim 10, wherein said pressure-sensing means comprises a pressure transducer having a first measuring gate connected to the first measuring tube and a second measuring gate connected to a surrounding atmosphere.

13. A device for determining open pressure for a patient's Eustachian tube which comprises:
    a first measuring tube having a proximal end for connection to the patient's nose and a distal end leading to a surrounding atmosphere,
    a plug closing said distal end of the first measuring tube,
    a second measuring tube having a proximal end for connection to the patient's ear,
    a pressure-measuring means for measuring air pressure in the first measuring tube,
    sound-generating means for generating a sound signal in the first measuring tube for propagation through the first measuring tube, the patient's nostril, nose cavity, Eustachian tube, middle ear, tympanic membrane and ear, and then into the second measuring tube, and
    a sound-detection means for sampling sound in the second measuring tube to determine whether the patient's Eustachian tube is blocked.

14. A device according to claim 13, wherein said sound-generating means is an electro-transducer.

15. A device according to claim 14, wherein said pressure-measuring means is a pressure transducer having a first measuring gate connected to the first measuring tube and a second measuring gate extending to the surrounding atmosphere.

* * * * *